United States Patent [19]

King et al.

[11] Patent Number: 5,021,575

[45] Date of Patent: Jun. 4, 1991

[54] METHOD FOR INTRODUCING A 1,2 DOUBLE BOND INTO AZASTEROIDS

[75] Inventors: Anthony O. King, Colonia; Robert K. Anderson, Plainsboro; Richard E. Shuman, Westfield; Leonard M. Weinstock, Belle Meade, all of N.J.

[73] Assignee: Merck & Co., Inc., Rahway, N.J.

[21] Appl. No.: 434,663

[22] Filed: Nov. 13, 1989

[51] Int. Cl.$^5$ ............................................. A61K 31/395
[52] U.S. Cl. ..................................................... 546/77
[58] Field of Search ........................... 546/77; 514/284

[56] References Cited

U.S. PATENT DOCUMENTS 4,220,775 9/1985 Rasmusson et al. ................. 546/77
4,377,584 3/1983 Rasmusson .......................... 424/258

FOREIGN PATENT DOCUMENTS 0155096 9/1985 European Pat. Off. .

OTHER PUBLICATIONS

Bhattacharya et al., JACS vol. 110, 3318(1988).
Back J. Org. Chem. vol. 46, 1442–1446(1981).
Rasmusson et al., J. Med. Chem. vol. 29, 2298–2315(1986).
Magnus et al., JACS, vol. 108, pp. 222–227(1986).
Back, T. G., J.C.S. Chem. Comm. 278–279(1978).

*Primary Examiner*—Nicholas S. Rizzo
*Attorney, Agent, or Firm*—Robert J. North; Charles M. Caruso

[57] ABSTRACT

A process for introducing a 1,2 double bond into a compound of the formula

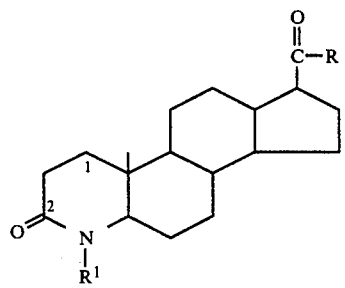

which comprises the process of (a) treating the compound of formula I with oxalyl chloride; (b) brominating the product of step (a) followed by in situ dehydrobromination; (c) deprotecting the product of step (b) to yield the $\alpha$ and $\beta$ isomers; (d) dehydrobrominating the product of step (c), which results in the introduction of a double bond at the 1,2 position.

10 Claims, No Drawings

METHOD FOR INTRODUCING A 1,2 DOUBLE BOND INTO AZASTEROIDS

BACKGROUND OF THE INVENTION

This invention is concerned with a process for dehydrogenating azasteroids, in particular 17β substituted 3-oxo-4 azasteroids, to provide the corresponding compound having a double bond at its 1,2 position.

Heretofore, azasteroids have been dehydrogenated to introduce a 1,2 double bond by means of benzene seleninic anhydride oxidation in which the saturated compound was heated with the benzene seleninic anhydride in refluxing chlorobenzene. Back, T. G., *J. Org. Chem.*, 46, 1442 (1981); Rasmussen et al., *J. Med. Chem.* 29, 2298 (1986), Dehydrogenation of azasteroids utilizing benzeneseleninic acid or benzene seleninic anhydride to form the corresponding Δ¹ compound is also discussed in Back, T. G., *J.C.S. Chem. Comm.*, 278–279 (1978). Additionally, sulfoxide elimination has been a process used to accomplish the dehydrogenation. See U.S. Pat. Nos. 4,377,584, 4,220,775 and EP application 85301122.9. However these reactions have been found to give poor yields, with a high degree of impurities and one requires the use of a selenium catalyst which is very expensive and is quite toxic.

It has also been known to dehydrogenate a 3-oxo-4-azalactam by a complicated 5-step process which involves a sulfenate intermediate. See Magnus et al., *J. Am. Chem.*, 108, 221–227 (1986). More recently, a dehydrogenation process involving a silylation-mediated DDQ oxidation of 4-aza-3-ketosteroids to the corresponding Δ¹-lactams has been developed. See Bhattacharya et al., *J. Am. Chem. Soc.*, 110, 3318 (1988).

The process of the present invention provides a method for introducing a 1,2 double bond into 17β-substituted 3-oxo-4 azasteroids via a four step process utilizing oxalyl chloride. The present invention provides a method to dehydrogenate a wide variety of compounds while avoiding the disadvantages of the prior art methods. These disadvantages include poor yields, expensive reagents, unwanted by-products and the use of toxic selenium catalysts.

SUMMARY OF THE INVENTION

The present invention provides a method for introducing a 1,2 double bond into a compound of the formula:

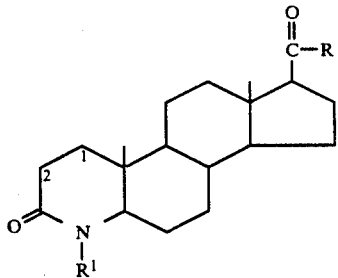

wherein
R is
(i) a straight or branched chain alkyl group having 1 to 12 carbons;
(ii) a straight or branched chain alkyl group having 1 to 12 carbons in which a hydrogen is substituted with a hydroxy, carboxylic acid or an alkyl ester having 1 to 4 carbons;
a cycloalkyl group having 4 to 8 carbons;
(iv) phenyl;
(v) $OR^1$ where $R^1$ is hydrogen or alkali metal, a $C_{1-8}$ straight or branched chain alkyl group or benzyl;
(vi) $NHR^2R^3$, where $R^2$ and $R^3$ are each independently selected from hydrogen, $C_{1-12}$ straight or branched chain alkyl, $C_{1-12}$ straight or branched chain alkyl having a hydrogen substituted with a hydroxy, carboxoylic acid or $C_{1-4}$ alkyl ester, $C_{3-10}$ cycloalkyl, phenyl, or $R^2$ and $R^3$ taken together with the nitrogen to which they are attached represent a 5-6 member saturated ring comprising up to one other heteroatom selected from oxygen and nitrogen;

$R^1$ is hydrogen, methyl, or ethyl;
by
(a) reacting the compound of formula I with oxalyl chloride to produce a compound of the formula:

II (b) reacting the compound of formula II with bromine to produce a compound of the formula:

III (c) reacting the compound of formula III with ethylenediamine to produce a compound of the formula:

IV (d) reacting the compound of formula IV with DBN or DBU to introduce a double bond at the 1,2 position of the compound of formula I.

The 4-azasteroid compounds prepared by the processes of the present invention are testosterone-5α-reductase inhibitors useful for treating the hyperandrogenic conditions of acne vulgaris, seborrhea, female hirsutism, androgenic alopecia including male pattern alopecia, prostatic carcinoma and benign prostatic hypertrophy by topical or systemic administration.

The schematic flow diagram which follows shows the processes of the present invention.

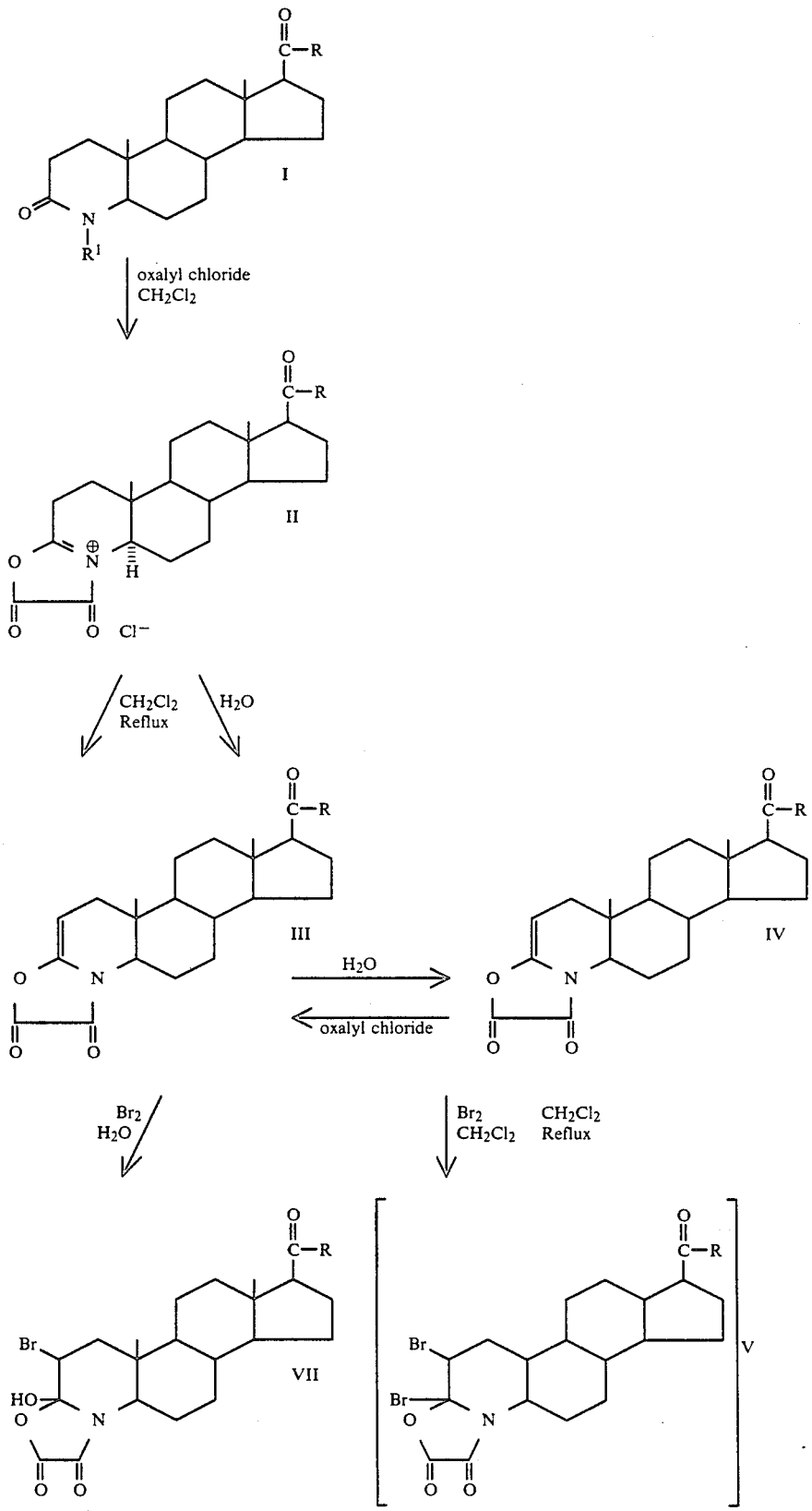

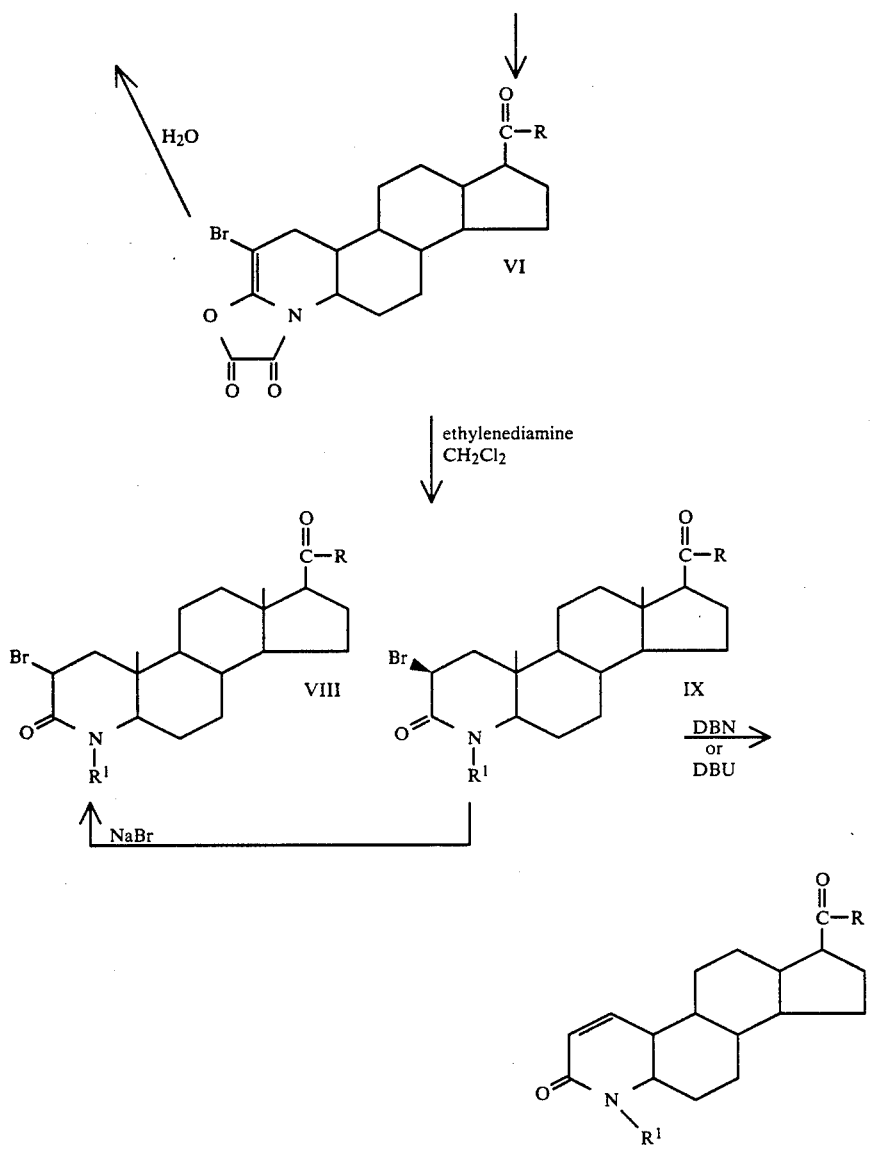

Generally, in the processes of the present invention both 5α-azamide and 5α-azamethylester are suitable in this three-steps one-pot process. Since all intermediates leading to products such as 2-bromo-5α-azasteroids are water sensitive, water should be vigorously excluded from the reaction. The reaction of oxalyl chloride with 5α-azasteroids in methylene chloride in the presence of an amine base such as diisopropylethylamine or pyridine gives vinylidenyloxazolidinediones. Other solvents such as chloroform and carbon tetrachloride can also be utilized. On bromination, vinylidinyloxazolidinediones are converted to dibromooxazolidinediones which are unstable and dehydrobrominate spontaneously in solution on warming to give bromovinylidinyloxazolidinediones. Reaction of ethylenediamine, N, N¹-dialkylethylenediaminos or 2 (methylamino) ethanol with bromovinylidineoxazolidinediones gives 2-bromo 5α-azasteroids as chemically stable and easily isolable products.

The dehydrobromination of 2 bromo-5α-azasteroids can be effected using potassium t-butoxide, DBN, DBU, tetrabutylammonium flouride, and N, N, N¹,N¹-tetramethylethylenediamine in THF, DMF and DMSO, but the yields of ¹Δ-5α-azasteroids vary substantially depending on starting 2-bromo-5α-azasteroids, dehydrobrominating agents, and solvents used. The best results were obtained using 2-bromo-5α-azaamide with potassium t-butoxide in DMF. The experimental procedure for this latter steroid is described below. The overall yield was 60%.

The following examples should be considered is not limiting the invention and will serve to illustrate the manner in which the present invention is accomplished. All temperatures are in °C.

EXAMPLE 1

Oxalylation/Bromination/De-Oxalylation

A 500ml three-neck round bottom flask equipped with a stirrer, a thermometer, a nitrogen inlet and a distillation condenser was charged with 5α-azaamide (10 g., 26.7 mmol), pyridine (26.7 ml) and methylene chloride (300 ml). The methylene chloride solution was distilled under atmospheric pressure until 100 ml of methylene chloride was collected. The reaction mixture was cooled to −70° C. and oxalyl chloride (2.56 ml, 29.4 mmol) was added dropwise over 10 min.

The mixture was warmed to 0° C. and aged at this temperature until the reaction wap complete and no 5α-azaamide was observed (1½ to 3 hrs.).

HPLC

Column: Dupont Zorbax C-8, 25 cm×4.6 mm
Solvent: 60% CH₃CN - 40% H₂O (0.1% H₃PO₄)
Flow: 1.5 ml/min
Wavelength: 210 nm
Detector: Kratos Spectroflow 757, AVFS=0.02
RT:
  5αAzaamide 4.6 min
  Vinylidenyloxazolidinedione Amide: 9.1/min
  3-Hydroxyoxazolidinedione Amide: 4.9 min.

Epsilon Caprolactam (0.226 g, 2 mmol) was added and the reaction further aged at 0° C. for ½ hour.

The mixture was then cooled to −70° C. and neat bromine (4.48 g, 28.0 mmol) was added. The reaction was aged for 15 minutes and then sampled and checked by HPLC to ensure that all vinylidineoxazolidinedione amide have been consumed. More bromine could be added in small portions if necessary to complete the bromination reaction.

HPLC

Same conditions as above.

RT:
  2-Bromo-3-hydroxyoxazolidinedione amide: 6.4 min, 6.7 min.
  2 Bromovinylidenyloxazolidinedione amide: 13.3 min.

The reaction mixture was warmed to 0° C. and aged (18-20 hrs) until all of the 2,3-dibromo-oxazolidinedione amides have converted to bromovinyloxazolidinedione amide. After cooling the mixture back to −65° C., 2-(methylamino) ethanol (9.02 g, 120.2 mmol) was added while maintaining the reaction temperature below −60° C.

The reaction was checked for the complete disappearance of the starting material by HPLC.

HPLC

Same conditions as reported above.

RT:
  2-Bromovinylidenyloxazolidinedione amide: 13.3 min.
  2-Bromo-5α-azaamide: 4.7 min & 5.0 min.

More 2-(methylamino) ethenol could be added in small portions (0.2 g) if the disappearance of bromovinylidineoxazolidinedione amide was not complete.

The mixture was warmed to room temperature and aged until the aminolthanol intermediate adducts have converted to 2-bromo-5α-azaamides (2 to 3 hours).

The solution was cooled to 0° C. and 200 ml of cold 2N HCL solution was added slowly while maintaining the temperature at ≦5° C. After the addition the two layers were thoroughly mixed and separated. The organic layer was washed again with 2N HCL (200 ml) followed by 10% brine (2×200 ml). To the methylene choloride solution was added acetonitrile (100 ml) and the methylene chloride was removed in vacuo at ≦40° C. while maintaining the liquid volume at ~35 ml by addition of acetonitrile.

When no more met.hylene chloride was detected in the distillate. the volume was further reduced to 35 ml of acetonitrile and the mixture was cooled to 0° C. Water (105 ml) was added slowly over 15 min. After aging for 1½ hours at 0° C., the solid was collected by filtration and the filter cake washed with water (50 ml). The filter cake was suction dried to a free flowing solid and then further dried at 60° C. in vacuo overnight (14 to 18 hours). The yield was 10.80 g, 85.1% corrected for 95.4 wt. % HPLC purity.

Dehydrobromination

In a 250 ml three-neck flask equipped with a stirrer, an internal thermometer, and a nitrogen inlet was charged potassium t-butoxide (6.15 g, 54.8 mmol) and 25 ml of dry DMF. After the potassium t-butoxide was completely dissolved, the mixture was cooled to 0° C. and a solution of 2-bromo 5α-azaamide (4.00 g, 8.8 mmol) in DMF (12 ml) was added dropwise while maintaining the temperature at 0° C.

After the addition was complete, the reaction was aged for an additional 10 min. and was then quenched by the dropwise addition of acetic acid (5.2 ml, 90 mmol) while keeping the temperature below 5° C. To the stirred solution was slowly added 200 ml of saturated sodium chloride. The suspension was stirred at 0° C. for 4 hours and the solid was isolated by filtration and washed with 200 ml of distilled water. The crude product was dried overnight in vacuo at 70° C. under a gentle nitrogen purge. The yield was 3.29 g, 80.2% corrected for 78.8% purity.

The crude MK906 was dissolved in isopropyl acetate (100 ml) with heating and the volume reduced to 15 ml by distillation under reduced pressure. The suspension was stirred overnight at 0° C. The solid was isolated by filtration and dried in the vacuum oven at 70° C. The yield was 2.16 g, 64.6% corrected for 95.4% purity.

The above solid was again dissolved in 10 ml of acetic acid and 100 ml of water was added slowly. The product gradually crystallized out of solution. The mixture was aged at r.t. for 10 hours with agitation. After filtration and drying at 70° C. in vacus, 1.97 g of white crystalline MK906 was obtained. The overall yield for the two steps was 60.2%, corrected for 98.0 wt. % purity.

HPLC

Same conditions as reported previously.

RT: MK906: 4.25 min.

What is claimed is:

1. A method of introducing a double bond at the 1,2 position of a compound having the formula:

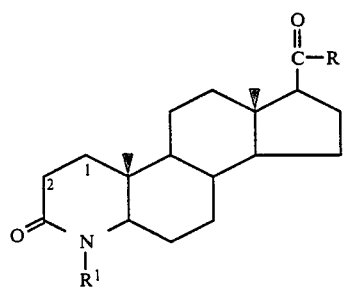

wherein

R is (i) a straight or branched chain alkyl group having 1 to 12 carbons;

(ii) a straight or branched chain alkyl group having 1 to 12 carbons in which a hydrogen is substituted with a hydroxy, carboxylic acid or an alkyl ester having 1 to 4 carbons;

(iii) a cycloalkyl group having 3 to 6 carbons;

(iv) phenyl;

(v) $OR^1$ where $R^1$ is hydrogen or alkali metal, a $C_{1-18}$ straight or branched chain alkyl group or benzyl;

(vi) $NHR^2R^3$, where $R^2$ and $R^3$ are each independently selected from hydrogen, $C_{1-12}$ straight or branched chain alkyl, $C_{1-12}$ straight or branched chain alkyl having a hydrogen substituted with ahydroxy, carboxylic acid or $C_{1-4}$ alkyl ester, $C_{3-10}$ cycloalkyl, phenyl, or $R^2$ and $R^3$ taken together with the nitrogen to which they are attached represent a 5-6 member saturated ring comprising up to one other heteroatom selected from oxygen and nitrogen;

$R^1$ is hydrogen, methyl, or ethyl;

which comprises the steps of:

(a) reacting the compound of formula I with oxalyl chloride in a dry inert organic solvent, in the presence of an amine, base at a temperature of about $-70°$ C. to $0°$ C., to produce a compound of the formula:

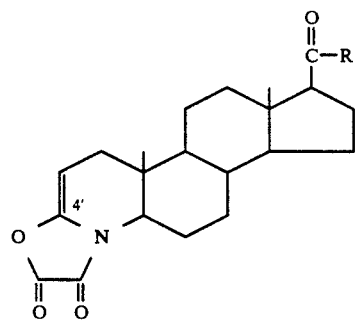

II (b) reacting the compound of formula II with bromine in a dry inert organic solvent at a temperature in the range of $-70°$ C. to $0°$ C., to produce a compound of the formula:

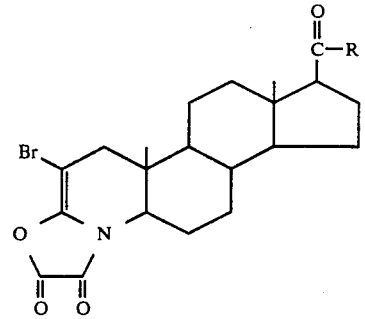

III (c) reacting the compound of formula III with ethylenediamien or 2-methylaminoethanol, in a dry inert organic solvent, at a temperature in the range of $-60°$ C. to $-65°$ C., to produce a compound of the formula:

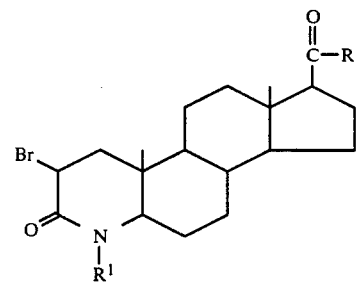

IV (d) reacting the compound of formula IV with DBN, DBU or potassium t-butoxide, in a dry inert organic solvent, at a temperature of about $0°$ C., to introduce a double bond at the 1,2 position of the compound of formula I.

2. The method of claim 1 wherein said compound of formula I is as follows:

| R | $R^1$ |
|---|---|
| NH-tert-butyl | H |
| iso-butyl | H |
| sec-butyl | H |
| phenyl | H. |

3. The method of claim 2 wherein R is NH-tert-butyl and $R^1$ is H.

4. The process of claim 1 wherein the solvent is the same for steps (a), (b) and (c).

5. The process of claim 4 wherein said solvent is methylene chloride.

6. The process of claim 1 wherein the amine base in step (a) is pyridine or diisopropylethylamine.

7. The process of claim 1 wherein step (d), 2-methylaminoethanol is utilized.

8. The process of claim 1 wherein the solvent for step (d) is dimethylformamide.

9. The process of claim 1 wherein potassium t-butoxide is utilized.

10. The process of claim 1 wherein step (a), the oxalyl chloride is reacted with the compound of formula I at about $-70°$ C. then warmed to $0°$ C.; step (b), the bromine is reacted with the compound of formula II at about $-70°$ C. and then warmed to $0°$ C.; step (c), 2-methylaminoethanol is reacted with the compound of formula III at about $-60°$ C. to $-65°$ C. and then warmed to $0°$ C.

* * * * *